(12) United States Patent
Surendranath et al.

(10) Patent No.: US 11,528,388 B2
(45) Date of Patent: Dec. 13, 2022

(54) NOISE SUPPRESSION IN A SAMPLING CIRCUIT

(71) Applicant: Texas Instruments Incorporated, Dallas, TX (US)

(72) Inventors: Nagesh Surendranath, Plano, TX (US); Sravana Kumar Goli, Bengaluru (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 223 days.

(21) Appl. No.: 16/928,248

(22) Filed: Jul. 14, 2020

(65) Prior Publication Data
US 2022/0021789 A1    Jan. 20, 2022

(51) Int. Cl.
*H04N 5/32*       (2006.01)
*H04N 5/378*      (2011.01)
*H04N 3/14*       (2006.01)
*G06G 7/186*      (2006.01)
*A61B 6/03*       (2006.01)
*H04N 5/345*      (2011.01)

(52) U.S. Cl.
CPC .......... *H04N 3/1568* (2013.01); *A61B 6/032* (2013.01); *G06G 7/186* (2013.01); *H04N 5/32* (2013.01); *H04N 5/3456* (2013.01); *H04N 5/378* (2013.01)

(58) Field of Classification Search
CPC ........ H04N 5/32; H04N 5/3456; H04N 5/378; H04N 5/3575; H04N 3/1568; A61B 6/032; G06G 7/186
See application file for complete search history.

(56) References Cited

U.S. PATENT DOCUMENTS

2009/0195680 A1*  8/2009  Krymski .............. G11C 27/024
                                                  348/300
2015/0268360 A1*  9/2015  Kumar .................. H04N 5/378
                                                  250/371

* cited by examiner

*Primary Examiner* — Nelson D. Hernández Hernández
(74) *Attorney, Agent, or Firm* — John R. Pessetto; Frank D. Cimino (57) ABSTRACT

In described examples, a circuit includes an integrator. The integrator receives an input signal. A first sampling network is coupled to the integrator and generates a signal voltage. A second sampling network is coupled to the integrator and generates a pixel sampled noise voltage. The pixel sampled noise voltage generated in a previous cycle is subtracted from the signal voltage generated in a current cycle to generate a true signal voltage.

20 Claims, 5 Drawing Sheets

NOISE SUPPRESSION IN A SAMPLING CIRCUIT

TECHNICAL FIELD

The present disclosure is generally related to sampling circuits, and more particularly to noise reduction in correlated multi-sampling circuit used in imaging applications.

BACKGROUND

Computed tomography (CT) is a medical imaging technique that produces three-dimensional images of internal human body parts from a large series of two-dimensional X-ray images (called profiles) taken in a single-axis rotating structure called a gantry. When compared to a conventional X-ray radiograph, which is an image of many planes superimposed on each other, a CT image exhibits significantly improved contrast.

With the advent of diagnostic imaging systems like CT, where complex and intensive image processing is required, semiconductors play a very important role in developing systems with increased density, flexibility and high performance. The helical or spiral CT machines that use faster computer systems and optimized software can continuously process the cross-section images while the object passes through the gantry at a constant speed.

X-ray slice data is generated using an X-ray source that rotates around the object, with multiple detectors positioned on the opposite side of the circle from the X-ray source. Many data scans are taken progressively as the patient/object is gradually passed through the gantry. An imaging system like CT includes multiple detectors, and each detector includes a photodiode and an AFE (analog front end).

A photodiode receives the X-rays attenuated by the patient and generates a corresponding current signal which is further converted to a digital signal by the AFE. The current signal generated is proportional to the energy of the photons received by the photodiode. The AFE includes an amplifier and a feedback capacitor. However, the amplifier has high bandwidth, and a large amount of power is required to drive the amplifier and to meet a given noise specification without degrading linearity.

SUMMARY

In described examples, a circuit includes an integrator. The integrator receives an input signal. A first sampling network is coupled to the integrator and generates a signal voltage. A second sampling network is coupled to the integrator and generates a pixel sampled noise voltage. The pixel sampled noise voltage generated in a previous cycle is subtracted from the signal voltage generated in a current cycle to generate a true signal voltage.

DETAILED DESCRIPTION OF EXAMPLE EMBODIMENTS

Figure 1:
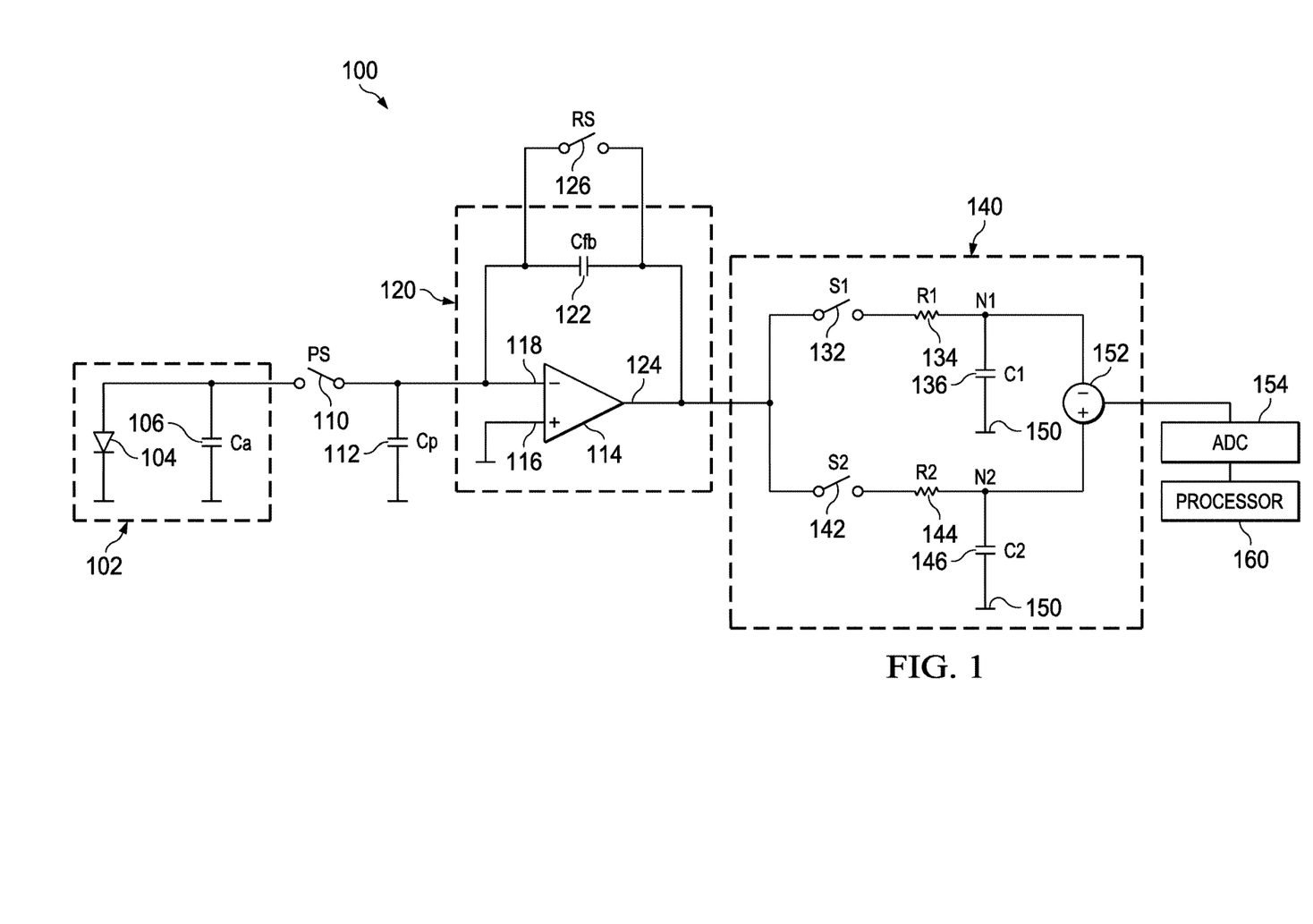
FIG. 1 is a block diagram illustrating a circuit.

FIG. 1 is a block diagram illustrating a circuit 100. The circuit 100 includes a photodiode 102, an integrator 120, a sampling network 140, an analog to digital converter (ADC) 154 and a processor 160. The photodiode 102 includes a sensor 104 and an associated capacitor Ca 106. The integrator 120 is coupled to the photodiode 102 through a pixel switch PS 110. The integrator 120 includes an amplifier 114 and a feedback capacitor Cfb 122. A parasitic capacitance Cp 112 is associated with the pixel switch PS 110. It is understood that the parasitic capacitor is represented for purpose of illustration and it represents input parasitic capacitance of the amplifier 114. The parasitic capacitance also develops because of routing on the board or PCB (printed circuit board) where the circuit 100 is placed. This parasitic capacitor is generally in the order of Pico farads.

The amplifier 114 includes an inverting terminal 118, a non-inverting terminal 116 and an output terminal 124. The feedback capacitor Cfb 122 is coupled between the inverting terminal 118 and the output terminal 124. A reset switch RS 126 is coupled in parallel to the feedback capacitor Cfb 122. The sampling network 140 is coupled to the integrator 120. The sampling network 140 includes a first switch S1 132, a first resistor R1 134, a first capacitor C1 136, a second switch S2 142, a second resistor R2 144, a second capacitor C2 146 and a subtractor 152.

The first switch S1 132 and the second switch S2 142 are coupled to the integrator 120. The first resistor R1 134 is coupled between the first switch S1 132 and a first node N1. The first capacitor C1 136 is coupled between the first node N1 and a ground terminal 150. The second resistor R2 144 is coupled between the second switch S2 142 and a second node N2. The second capacitor C2 146 is coupled between the second node N2 and the ground terminal 150. The subtractor 152 is coupled to the first node N1 and the second node N2. The ADC 154 is coupled to the subtractor 152, and the processor 160 is coupled to the ADC 154.

The operation of the circuit 100 illustrated in FIG. 1 is explained now. The circuit 100 operates in a reset phase, an offset phase and a signal phase. In the reset phase, the reset switch RS 126 is closed, and the pixel switch PS 110, the first switch S1 132 and the second switch S2 142 are opened. The reset phase is used to reset the feedback capacitor Cfb 122 and to discharge any accumulated charge in the feedback capacitor Cfb 122.

In the offset phase, the reset switch RS 126 is opened. A residual noise is sampled on the feedback capacitor Cfb 122 which generates a sampled reset noise voltage at the output terminal 124 of the amplifier 114. The sampled reset noise voltage represents a sampled reset noise of the feedback capacitor Cfb 122 and the reset switch RS 126. The pixel switch PS 110 and the second switch S2 142 are opened. The first switch S1 132 is closed. The sampled reset noise voltage is sampled on the first capacitor C1 136. Henceforth, a voltage generated at the first node N1 is the sampled reset noise voltage.

In the signal phase, the reset switch RS 126 remains open. The first switch S1 132 is opened, and the pixel switch PS 110 and the second switch S2 142 are closed. The photodiode 102 generates an input signal in response to received light pulses. The sensor 104 in the photodiode 102 receives the light pulses, and the associated capacitor Ca 106 stores the input signal generated in response to the received light pulses.

The input signal from the photodiode 102 is provided to the integrator 120 which generates a first voltage. The first voltage is a sum of the input signal and the sampled reset noise voltage. The first voltage is sampled on the second capacitor C2 146. Thus, a voltage at the second node N2 is the first voltage. The subtractor 152 receives the sampled reset noise voltage at the first node N1 and the first voltage at the second node N2. The subtractor 152 subtracts the sampled reset noise voltage from the first voltage to generate a signal voltage. Thus, the signal voltage does not include the sampled reset noise of the feedback capacitor Cfb 122 and the reset switch RS 126. The ADC 154 generates a digital signal in response to the signal voltage, and the processor 160 stores and processes the digital signal received from the ADC 154.

The reset phase, the offset phase and the signal phase constitute a cycle, and a cycle spans for a frame time T. After the signal phase, the pixel switch PS 110 is opened to reset the feedback capacitor Cfb 122 without disturbing a charge getting accumulated on the associated capacitor Ca 106. A noise associated with the pixel switch PS 110 and a noise associated with the integrator 120 is sampled on the associated capacitor Ca 106. This noise is called as pixel sampled noise, and a voltage associated with the pixel sampled noise is pixel sampled noise voltage. The associated capacitor Ca 106 stores the pixel sampled noise voltage. The pixel sampled noise voltage gets added to the signal voltage generated responsive to a subsequent cycle. This degrades the SNR (signal to noise ratio) of the circuit 100.

In the offset phase, a noise generated by the amplifier 114 is mitigated by the combination of the first resistor R1 134 and the first capacitor C1 136. Similarly, a noise generated by the amplifier 114 in the signal phase is mitigated by the combination of the second resistor R2 144 and the second capacitor C2 146. A noise generated at the first node N1 is corresponds to the sampled reset noise voltage, and a noise generated at the second node N2 corresponds to a sum of the sampled reset noise voltage and a pixel sampled noise voltage generated in a previous cycle. The sampled reset noise voltage is mitigated by the subtractor 152 in the sampling network 140. However, the pixel sampled noise voltage generated in the previous cycle is not addressed in the circuit 100 and hence degrades the performance of the circuit 100.

The pixel sampled noise is a function of bandwidth of the amplifier 114, the associated capacitor Ca 106 and the parasitic capacitance Cp 112. When the bandwidth of the amplifier 114 is large, the pixel sampled noise is also large. In order to reduce the pixel sampled noise, one option is to reduce power spectral density of an input noise of the circuit 100, and the second option is to reduce the bandwidth of the amplifier 114. The circuit 100 will need higher power to reduce the power spectral density of the input noise. Also, the circuit 100 may implement dynamic bandwidth switching of the amplifier 114. However, this introduces non-linearity at the instants of bandwidth switching. In addition, reducing bandwidth of the amplifier 114 may require a bigger compensation capacitor which increases the area of the circuit 100. In a case when the amplifier 114 is considered ideal with very low bandwidth, the pixel sampled noise will approach a fundamental limit set by the associated capacitor Ca 106 and the parasitic capacitance Cp 112. Thus, the circuit 100 is not able to address the problem of pixel sampled noise, and this pixel sampled noise degrades the noise performance of the circuit 100 based on values of multiple parameters including, but not limited to, bandwidth of the amplifier 114, the pixel switch PS 110, the parasitic capacitance Cp 112 and the associated capacitor Ca 106.

Figure 2:
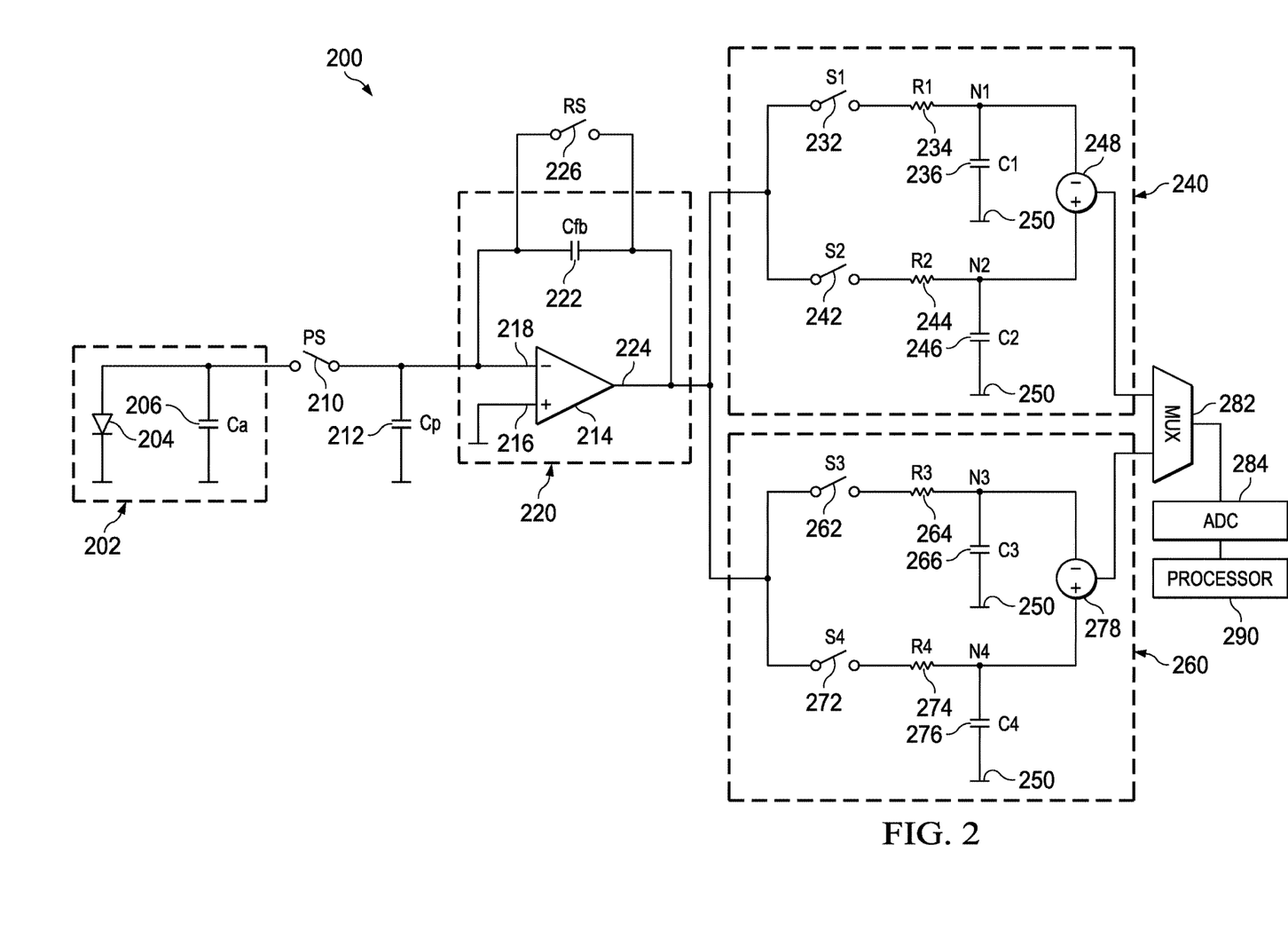
FIG. 2 is a block diagram illustrating a circuit, according to an embodiment.

FIG. 2 is a block diagram illustrating a circuit 200, according to an embodiment. The circuit 200 includes a photodiode 202, an integrator 220, a first sampling network 240, a second sampling network 260, a multiplexer 282, an analog to digital converter (ADC) 284 and a processor 290. The photodiode 202 includes a sensor 204 and an associated capacitor Ca 206. The integrator 220 is coupled to the photodiode 202 through a pixel switch PS 210. The integrator 220 includes an amplifier 214 and a feedback capacitor Cfb 222. A parasitic capacitance Cp 212 is associated with the pixel switch PS 210. It is understood that the parasitic capacitor is represented for purpose of illustration and it represents input parasitic capacitance of the amplifier 214. The parasitic capacitance also develops because of routing on the board or PCB where the circuit 200 is placed. This parasitic capacitor is generally in the order of Pico farads.

The amplifier 214 includes an inverting terminal 218, a non-inverting terminal 216 and an output terminal 224. In one example, the non-inverting terminal 216 receives a secondary voltage. In another example, the non-inverting terminal 216 is coupled to a ground terminal. The feedback capacitor Cfb 222 is coupled between the inverting terminal 218 and the output terminal 224. A reset switch RS 226 is coupled in parallel to the feedback capacitor Cfb 222. The first sampling network 240 is coupled to the integrator 220. The first sampling network 240 includes a first switch S1 232, a first resistor R1 234, a first capacitor C1 236, a second switch S2 242, a second resistor R2 244 and a second capacitor C2 246.

The first switch S1 232 and the second switch S2 242 are coupled to the integrator 220. The first resistor R1 234 is coupled between the first switch S1 232 and a first node N1. The first capacitor C1 236 is coupled between the first node N1 and a ground terminal 250. The second resistor R2 244 is coupled between the second switch S2 242 and a second node N2. The second capacitor C2 246 is coupled between the second node N2 and the ground terminal 250. A first subtractor 248 is coupled to the first node N1 and the second node N2.

The second sampling network 260 is coupled to the integrator 220. The second sampling network 260 includes a third switch S3 262, a third resistor R3 264, a third capacitor C3 266, a fourth switch S4 272, a fourth resistor R4 274 and a fourth capacitor C4 276. The third switch S3 262 and the fourth switch S4 272 are coupled to the integrator 220. The third resistor R3 264 is coupled between the third switch S3 262 and a third node N3. The third capacitor C3 266 is coupled between the third node N3 and the ground terminal 250.

The fourth resistor R4 274 is coupled between the fourth switch S4 272 and a fourth node N4. The fourth capacitor C4 276 is coupled between the fourth node N4 and the ground terminal 250. A second subtractor 278 is coupled to the third node N3 and the fourth node N4. The multiplexer 282 is coupled to the first subtractor 248 and the second subtractor 278. The ADC 284 is coupled to the multiplexer 282, and the processor 290 is coupled to the ADC 284. The circuit 200 may include one or more conventional components that are not discussed here for simplicity of the description.

The operation of the circuit 200 illustrated in FIG. 2 is explained now. The circuit 200 operates in a reset phase, an offset phase, a signal phase and a delayed signal phase. In the reset phase, the reset switch RS 226 is closed, the first switch S1 232, the second switch S2 242, and the third switch S3 262 are opened. The pixel switch PS 210 and the fourth switch S4 272 are opened in the delayed signal phase and remains open in the reset phase. The reset phase is used to reset the feedback capacitor Cfb 222 and to discharge any accumulated charge in the feedback capacitor Cfb 222.

In the offset phase, the reset switch RS 226 is opened. A residual noise is sampled on the feedback capacitor Cfb 222 which generates a sampled reset noise voltage at the output terminal 224 of the amplifier 214. The sampled reset noise voltage represents a sampled reset noise of the feedback capacitor Cfb 222 and the reset switch RS 226. The pixel switch PS 210, the second switch S2 242, the third switch S3 262 and the fourth switch S4 272 are opened. The first switch S1 232 is closed. The sampled reset noise voltage is sampled on the first capacitor C1 236. Henceforth, a voltage generated at the first node N1 is the sampled reset noise voltage.

In the signal phase, the reset switch RS 226 remains open. The first switch S1 232 is opened, and the pixel switch PS 210, the second switch S2 242, the third switch S3 262 and the fourth switch S4 272 are closed. The photodiode 202 generates an input signal in response to received light pulses. The sensor 204 in the photodiode 202 receives the light pulses, and the associated capacitor Ca 206 stores the input signal generated in response to the received light pulses.

The input signal from the photodiode 202 is provided to the integrator 220 which generates a first voltage. The first voltage is a sum of the input signal and the sampled reset noise voltage. The first voltage is sampled on the second capacitor C2 246, the third capacitor C3 266 and the fourth capacitor C4 276. The second switch S2 242 and the third switch S3 262 are opened at the end of the signal phase. Thus, a voltage at each of the second node N2 and the third node N3 is the first voltage.

In the delayed signal phase, the pixel switch PS 210 is opened. The integrator 220 generates a second voltage. The second voltage is sampled on the fourth capacitor C4 276. The fourth switch S4 272 is opened.

In the first subtractor 248, the sampled reset noise voltage at the first node N1 is subtracted from the first voltage at the second node N2 to generate a signal voltage by the first sampling network 240. Thus, the signal voltage does not include the sampled reset noise of the feedback capacitor Cfb 222 and the reset switch RS 226. In the second subtractor 278, the first voltage at the third node N3 is subtracted from the second voltage at the fourth node N4 to generate a pixel sampled noise voltage by the second sampling network 260.

The pixel sampled noise voltage is proportional to a noise associated with the integrator 220 and a noise associated with the pixel switch PS 210. Also, the second voltage is a sum of the first voltage and the pixel sampled noise voltage. The signal voltage from the first subtractor 248 and the pixel sampled noise voltage from the second subtractor 278 are provided to the multiplexer 282. The multiplexer provides these signals to the ADC 284. The ADC 284 generates a first digital signal in response to the signal voltage. The ADC 284 generates a second digital signal in response to the pixel sampled noise voltage. The processor 290 stores the first and second digital signal. The processor 290 subtracts the second digital signal generated in a previous cycle from the first digital signal generated in a current cycle to generate a true signal voltage. In one example, the pixel sampled noise voltage generated in a current cycle is subtracted from the signal voltage generated in the subsequent cycle using analog circuitry. The use of analog circuitry avoids conversion of signals to digital format and the process of performing such subtraction in the processor 290.

The reset phase, the offset phase, the signal phase and the delayed signal phase constitute a cycle, and a cycle spans for a frame time T. After the delayed signal phase, the pixel switch PS 210 is opened to reset the feedback capacitor Cfb 222 without disturbing a charge getting accumulated on the associated capacitor Ca 206. A noise associated with the pixel switch PS 210 and a noise associated with the integrator 220 is sampled on the associated capacitor Ca 206. This noise is called as pixel sampled noise, and a voltage associated with the pixel sampled noise is pixel sampled noise voltage. The associated capacitor Ca 206 stores the pixel sampled noise voltage. The pixel sampled noise voltage gets added to the signal voltage generated corresponding to a subsequent cycle. Hence, the circuit 200 provides for cancellation of this pixel sampled noise. The circuit 200 enables the processor 290 to cancel the pixel sampled noise voltage generated in a previous cycle to be subtracted from the signal voltage generated in a current cycle. This improves the SNR (signal to noise ratio) of the circuit 200 as compared to the SNR of the circuit 100.

In the offset phase, a noise generated by the amplifier 214 is mitigated by the combination of the first resistor R1 234 and the first capacitor C1 236. Similarly, a noise generated by the amplifier 214 in the signal phase is mitigated by the combination of the second resistor R2 244 and the second capacitor C2 246. A noise generated at the first node N1 corresponds to the sampled reset noise voltage. A noise generated at the second node N2 and the third node N3 corresponds to a sum of the sampled reset noise voltage and the pixel sampled noise voltage generated in a previous cycle. A noise generated at the third node N4 corresponds to a sum of the sampled reset noise voltage, the pixel sampled noise voltage generated in a previous cycle and the pixel sampled noise voltage generated in a current cycle. The sampled reset noise voltage is mitigated by the first subtractor 248 in the first sampling network 240 which generates the signal voltage. The pixel sampled noise voltage generated in the current cycle is obtained from the second subtractor 278 in the second sampling network 260. This pixel sampled noise voltage corresponding to the current cycle is subtracted from the signal voltage generated corresponding to the subsequent cycle to generate a true signal voltage. This improves the performance of the circuit 200.

The pixel sampled noise is a function of bandwidth of the amplifier 214, the associated capacitor Ca 206 and the parasitic capacitance Cp 212. When the bandwidth of the amplifier 214 is large, the pixel sampled noise is also large. The circuit 200 provides for cancellation of pixel sampled noise without reducing the power spectral density of an input noise of the circuit 200. The reduction in power spectral density would otherwise require burning more power in the circuit 200.

The circuit 200 addresses the problem of pixel sampled noise without reducing the bandwidth of the amplifier 214. The bandwidth reduction of the amplifier 214 comes with multiple problems including non-linearity and increased area. Hence, the circuit 200 effectively eliminates the problem of pixel sampled noise by using a second sampling network 260. The delayed signal phase allows sampling of the pixel sampled noise on the fourth capacitor C4 276 in the second sampling network 260. The corresponding pixel sampled noise voltage generated in the previous cycle is subtracted from the signal voltage generated in the current cycle to generate the true signal voltage. This improves the noise performance of the circuit 200.

Figure 3:
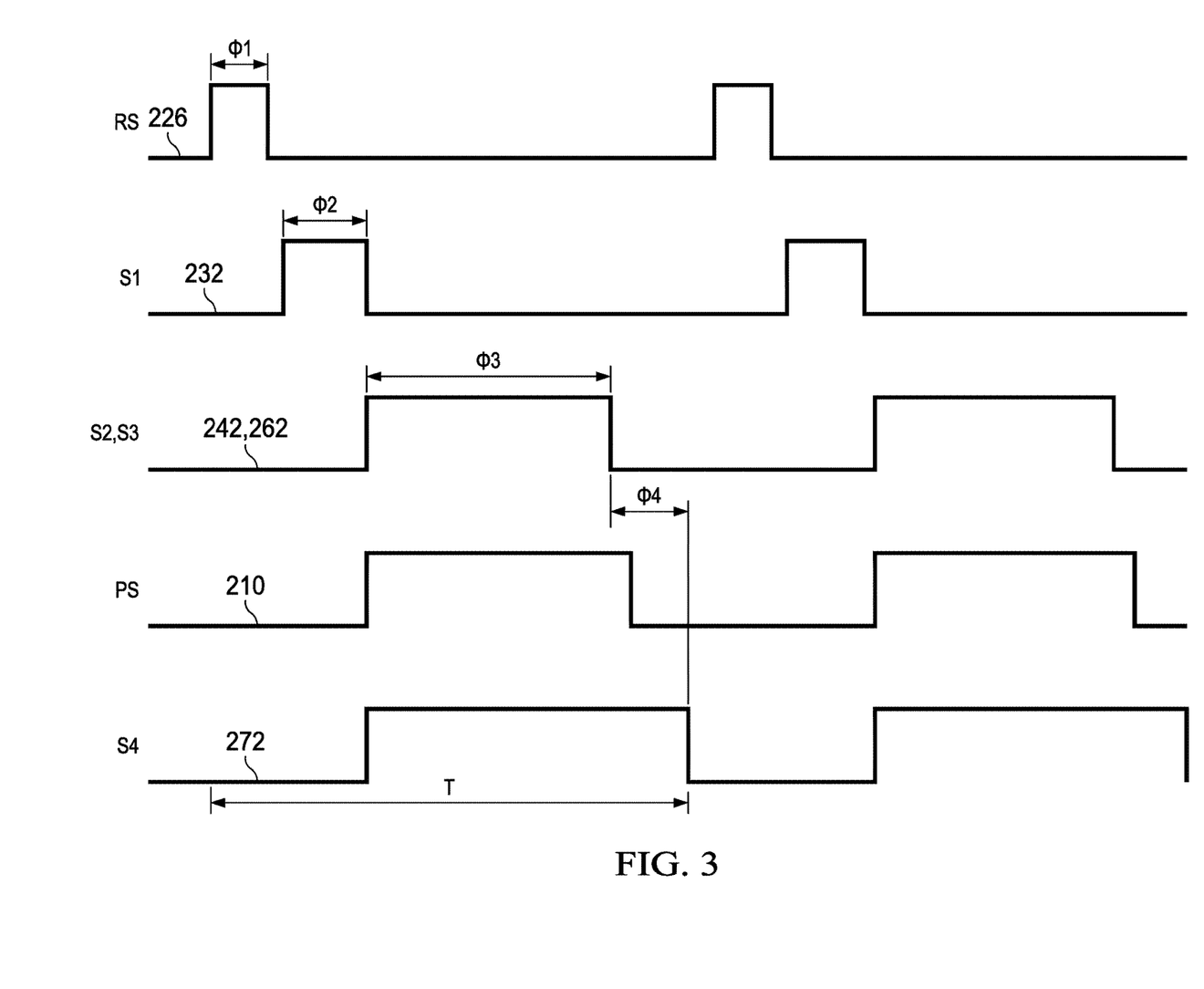
FIG. 3 is a timing diagram illustrating operation of the circuit 200, according to an embodiment.

FIG. 3 is a timing diagram illustrating operation of the circuit 200 in FIG. 2, according to an embodiment. The timing diagram illustrates the various phases of operation of the circuit 200. The timing diagram is explained in connection with the operation of circuit 200 in FIG. 2. Φ1 represents the reset phase. In the reset phase, the reset switch RS 226 is closed, the first switch S1 232, the second switch S2 242, and the third switch S3 262 are opened. The pixel switch PS 210 and the fourth switch S4 272 are opened in the delayed signal phase and remains open in the reset phase. The reset phase is used to reset the feedback capacitor Cfb 222 and to discharge any accumulated charge in the feedback capacitor Cfb 222.

Φ2 represent the offset phase. In the offset phase, the reset switch RS 226 is opened. A residual noise is sampled on the feedback capacitor Cfb 222 which generates a sampled reset noise voltage at the output terminal 224 of the amplifier 214. The sampled reset noise voltage represents a sampled reset noise of the feedback capacitor Cfb 222 and the reset switch RS 226. The pixel switch PS 210, the second switch S2 242, the third switch S3 262 and the fourth switch S4 272 are opened. The first switch S1 232 is closed. The sampled reset noise voltage is sampled on the first capacitor C1 236. Henceforth, a voltage generated at the first node N1 is the sampled reset noise voltage.

Φ3 represent the signal phase. In the signal phase, the reset switch RS 226 remains open. The first switch S1 232 is opened, and the pixel switch PS 210, the second switch S2 242, the third switch S3 262 and the fourth switch S4 272 are closed. The photodiode 202 generates an input signal in response to received light pulses. The sensor 204 in the photodiode 202 receives the light pulses, and the associated capacitor Ca 206 stores the input signal generated in response to the received light pulses.

The input signal from the photodiode 202 is provided to the integrator 220 which generates a first voltage. The first voltage is a sum of the input signal and the sampled reset noise voltage. The first voltage is sampled on the second capacitor C2 246, the third capacitor C3 266 and the fourth capacitor C4 276. The second switch S2 242 and the third switch S3 262 are opened. Thus, a voltage at each of the second node N2 and the third node N3 is the first voltage.

Φ3 represent the delayed signal phase. In the delayed signal phase, the pixel switch PS 210 is opened. The integrator 220 generates a second voltage. The second voltage is sampled on the fourth capacitor C4 276. The fourth switch S4 272 is opened.

The first subtractor 248 in circuit 200 subtracts the sampled reset noise voltage at the first node N1 from the first voltage at the second node N2 to generate a signal voltage. Thus, the signal voltage does not include the sampled reset noise of the feedback capacitor Cfb 222 and the reset switch RS 226. The second subtractor 278 subtracts the first voltage at the third node N3 from the second voltage at the fourth node N4 to generate a pixel sampled noise voltage by the second sampling network 260.

The reset phase Φ1, the offset phase Φ2, the signal phase Φ3 and the delayed signal phase Φ4 constitute a cycle, and a cycle spans for a frame time T. After the delayed signal phase Φ4, the pixel switch PS 210 is opened to reset the feedback capacitor Cfb 222 without disturbing a charge getting accumulated on the associated capacitor Ca 206. A noise associated with the pixel switch PS 210 and the noise associated with the integrator 220 is sampled on the associated capacitor Ca 206. This noise is called as pixel sampled noise, and a voltage associated with the pixel sampled noise is pixel sampled noise voltage. The associated capacitor Ca 206 stores the pixel sampled noise voltage.

The pixel sampled noise voltage gets added to the signal voltage generated corresponding to a subsequent cycle. The circuit 200 provides for cancellation of this pixel sampled noise. The signal voltage from the first subtractor 248 and the pixel sampled noise voltage from the second subtractor 278 are provided to the multiplexer 282. The multiplexer provides these signals to the ADC 284. The ADC 284 generates a first digital signal in response to the signal voltage. The ADC 284 generates a second digital signal in response to the pixel sampled noise voltage. The processor 290 stores the first and second digital signal. The processor 290 subtracts the second digital signal generated in a previous cycle from the first digital signal generated in a current cycle to generate a true signal voltage.

Thus, the circuit 200 enables the processor 290 to cancel the pixel sampled noise voltage generated in a previous cycle to be subtracted from the signal voltage generated in a current cycle. This improves the SNR (signal to noise ratio) of the circuit 200 as compared to the SNR of the circuit 100.

Figure 4:
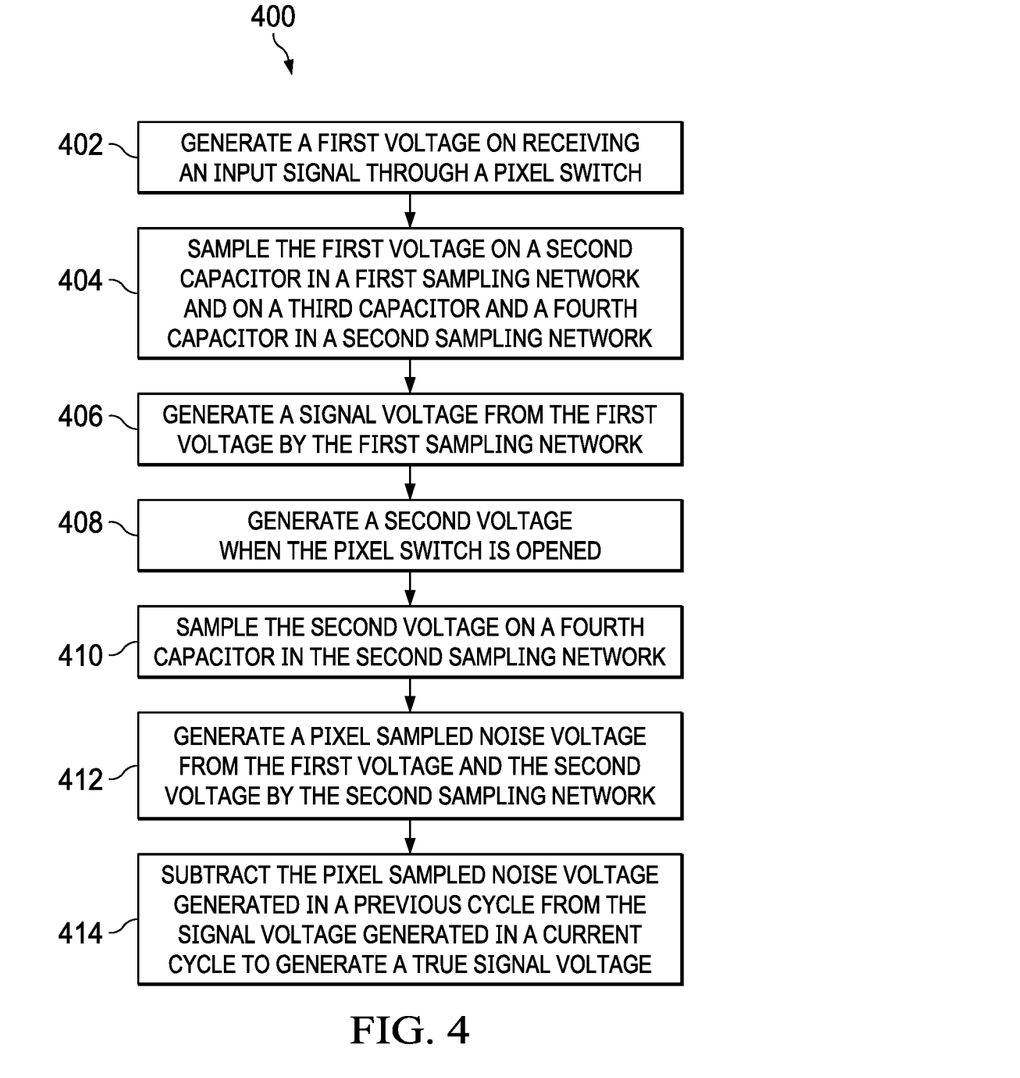
FIG. 4 is a flowchart to illustrate a method of operation of a circuit, according to an embodiment.

FIG. 4 is a flowchart 400 to illustrate a method of operation of a circuit, according to an embodiment. The flowchart 400 is explained in connection with the circuit 200 illustrated in FIG. 2. At step 402, a first voltage is generated on receiving an input signal through a pixel switch. In circuit 200, the photodiode 202 generates the input signal in response to received light pulses. The sensor 204 in the photodiode 202 receives the light pulses, and the associated capacitor Ca 206 stores the input signal generated in response to the received light pulses. The input signal from the photodiode 202 is provided to the integrator 220 which generates the first voltage.

At step 404, the first voltage is sampled on a first capacitor in a first sampling network and on a third capacitor and on a fourth capacitor in a second sampling network. The first voltage is sampled on the second capacitor C2 246 in the first sampling network 240. The first voltage is also sampled on the third capacitor C3 266 and the fourth capacitor C4 276 in the second sampling network 260. The second switch S2 242 and the third switch S3 262 are opened. Thus, a voltage at each of the second node N2 and the third node N3 is the first voltage.

At step 406, a signal voltage is generated from the first voltage by the first sampling network. In circuit 200, the signal voltage is generated by the first sampling network 240. A second voltage is generated when the pixel switch is opened, at step 408. The second voltage is sampled on a fourth capacitor in the second sampling network, at step 410. In circuit 200, during the delayed signal phase, the pixel switch PS 210 is opened. The integrator 220 generates the second voltage. The second voltage is sampled on the fourth capacitor C4 276. The fourth switch S4 272 is opened.

At step 412, a pixel sampled noise voltage is generated by the second sampling network from the first voltage and the second voltage. The second subtractor 278 in the second sampling network 260 subtracts the first voltage at the third node N3 from the second voltage at the fourth node N4 to generate the pixel sampled noise voltage. The second voltage is a sum of the first voltage and a pixel sampled noise voltage. The pixel sampled noise voltage is proportional to a noise associated with the integrator 220 and a noise associated with the pixel switch PS 210.

At step 414, the pixel sampled noise voltage generated in a previous cycle is subtracted from the signal voltage generated in a current cycle to generate a true signal voltage.

The ADC 284 in circuit 200 generates a first digital signal and a second digital signal in response to the signal voltage and the pixel sampled noise voltage respectively. The processor 290 subtracts the second digital signal generated in the previous cycle from the first digital signal generated in the current cycle to generate the true signal voltage.

Thus, the method illustrated by flowchart 400 provides for cancellation of the pixel sampled noise. The pixel sampled noise is a function of bandwidth of the amplifier 214, the associated capacitor Ca 206 and the parasitic capacitance Cp 212. When the bandwidth of the amplifier 214 is large, the pixel sampled noise is also large. The method illustrated by flowchart 400 provides for cancellation of pixel sampled noise without reducing the power spectral density of an input noise of the circuit 200. The reduction in power spectral density would otherwise require burning more power in the circuit 200.

The method illustrated by flowchart 400 addresses the problem of pixel sampled noise without reducing the bandwidth of the amplifier 214. The bandwidth reduction of the amplifier 214 comes with multiple problems including non-linearity and increased area. Hence, the method effectively eliminates the problem of pixel sampled noise by using the second sampling network 260. The delayed signal phase allows sampling of the pixel sampled noise on the fourth capacitor C4 276 in the second sampling network 260. The corresponding pixel sampled noise voltage generated in the previous cycle is subtracted from the signal voltage generated in the current cycle to generate the true signal voltage. This improves the noise performance of the circuit 200.

Figure 5:
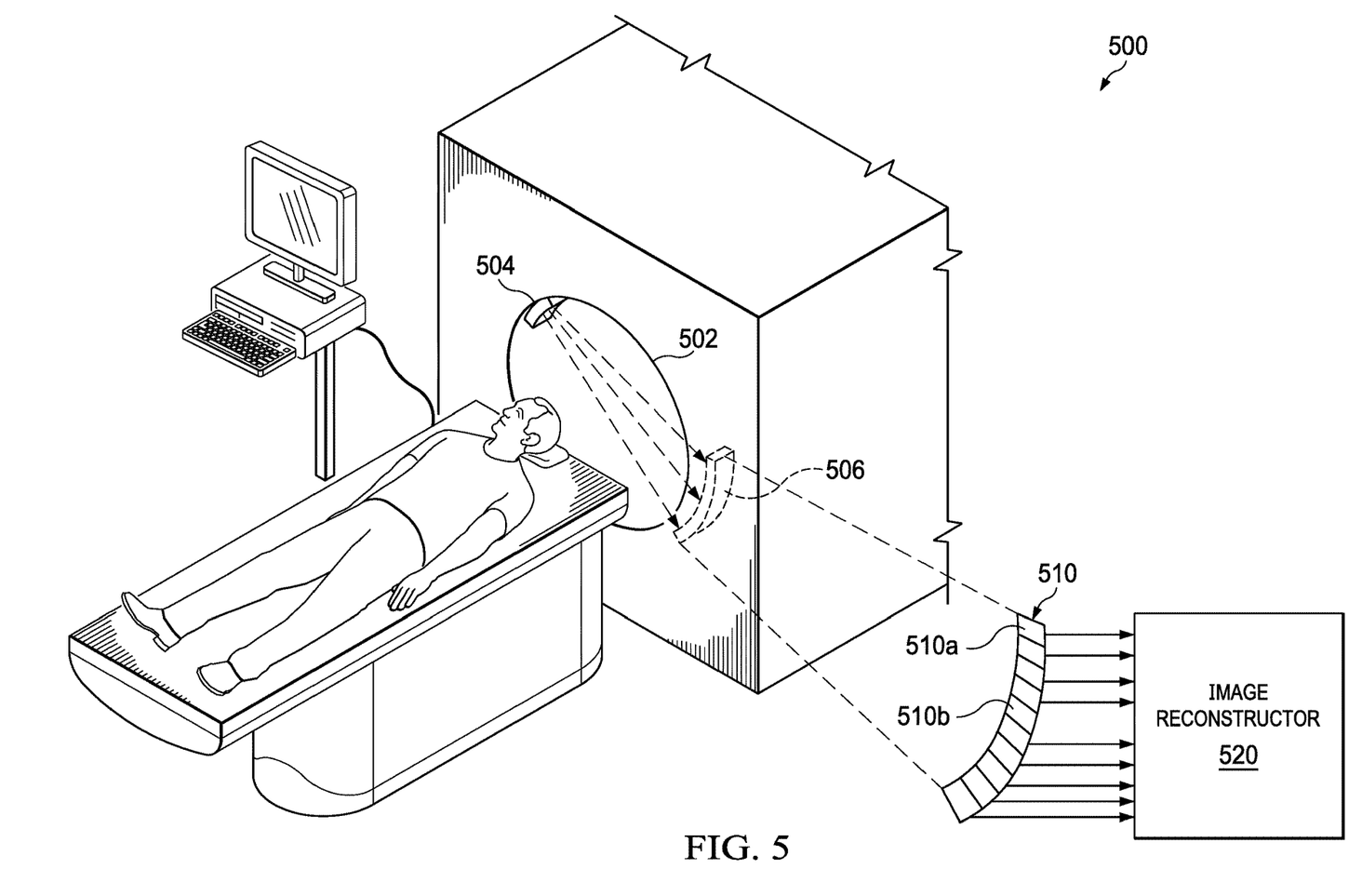
FIG. 5 illustrates an imaging system, according to an embodiment.

FIG. 5 illustrates an imaging system 500, according to an embodiment. The imaging system 500, in one version, is a CT (computed tomography) imaging system. The imaging system 500 includes a gantry 502 that receives an object, a living organism and/or a patient. The gantry 502 rotates at a defined speed. In one example, a controller provides the defined speed to the gantry 502.

An x-ray source 504 is disposed in the gantry 502. The x-ray source 504 emits x-rays towards the patient. The x-rays pass through the patient and are attenuated by the patient and received by a receiver 506. Many scans are taken progressively as the patient/object is gradually passed through the gantry. A cross-section of the receiver 506 is enlarged and illustrated for better clarity. The cross-section includes a plurality of detectors 510.

The plurality of detectors 510 receives x-rays attenuated by the patient. The plurality of detectors 510 includes detectors 510a and 510b. At least one detector of the plurality of detectors 510 generates a current signal in response to the received attenuated x-rays. At least one detector is similar to the circuit 200 (illustrated in FIG. 2) in connection and operation. In one example, the detector 510b is similar to the circuit 200 in connection and operation. The photodiode in the detector 510b generates the current signal in response to the received attenuated x-rays from the patient.

The detector 510b similar to the circuit 200 includes a photodiode, a pixel switch, an integrator, a first sampling network, a second sampling network, a multiplexer, an analog to digital converter (ADC) and a processor. The detector 510b operates in a reset phase, an offset phase, a signal phase and a delayed signal phase.

A noise associated with the pixel switch and a noise associated with the integrator is called as pixel sampled noise, and a voltage associated with the pixel sampled noise is pixel sampled noise voltage. The pixel sampled noise voltage gets added to a signal voltage generated corresponding to a subsequent cycle. The detector 510b provides for cancellation of this pixel sampled noise. The detector 510b cancels the pixel sampled noise voltage generated in a previous cycle from the signal voltage generated in a current cycle. This improves the SNR (signal to noise ratio) of the detector 510b.

The detector 510b provides for cancellation of pixel sampled noise without reducing the power spectral density of an input noise of the detector 510b. The reduction in power spectral density would otherwise require burning more power in the detector 510b. The detector 510b addresses the problem of pixel sampled noise without reducing the bandwidth of an amplifier used in the integrator. The bandwidth reduction of the amplifier comes with multiple problems including non-linearity and increased area. Hence, the detector 510b effectively eliminates the problem of pixel sampled noise by using the second sampling network. The delayed signal phase allows sampling of the pixel sampled noise on the second sampling network 260. The corresponding pixel sampled noise voltage generated in the previous cycle is subtracted from the signal voltage generated in the current cycle to generate the true signal voltage. This improves the noise performance of the detector 510b.

The image reconstructor 520 receives the digital signal from each detector of the plurality of detectors 510 to create an image of a part of patient which is being scanned by the imaging system 500. In one example, the multiplexer, the ADC and the processor in the detector 510b are part of the image reconstructor 520. The image reconstructor 520, in one example, includes a processor. The processor can be, for example, a CISC-type (Complex Instruction Set Computer) CPU, RISC-type CPU (Reduced Instruction Set Computer), or a digital signal processor (DSP). The image reconstructor 520, in one example, is disposed outside the imaging system 500. The imaging system 500 may include one or more conventional components that are not discussed here for simplicity of the description.

Modifications are possible in the described embodiments, and other embodiments are possible, within the scope of the claims.

What is claimed is:

1. A circuit comprising:
   an integrator configured to receive an input signal;
   a first sampling network coupled to the integrator and configured to generate a signal voltage, the first sampling network having a first capacitor and a second capacitor; and
   a second sampling network coupled to the integrator and configured to generate a pixel sampled noise voltage, the second sampling network having a third capacitor and a fourth capacitor, wherein the pixel sampled noise voltage generated in a previous cycle is subtracted from the signal voltage generated in a current cycle to generate a true signal voltage.

2. The circuit of claim 1, wherein the integrator comprises:
   an inverting terminal of an amplifier configured to receive the input signal;
   a non-inverting terminal of the amplifier configured to receive a secondary voltage; and
   a feedback capacitor coupled between the inverting terminal and an output terminal of the amplifier.

3. The circuit of claim 2 further comprising a reset switch coupled in parallel to the feedback capacitor.

4. The circuit of claim 3, wherein the first sampling network comprises:
   a first switch coupled to the integrator;

a first resistor coupled between the first switch and a first node, the first capacitor coupled between the first node and a ground terminal;
a second switch coupled to the integrator;
a second resistor coupled between the second switch and a second node, the second capacitor coupled between the second node and the ground terminal; and
a first subtractor coupled to the first node and the second node.

5. The circuit of claim 4, wherein the second sampling network comprises:
a third switch coupled to the integrator;
a third resistor coupled between the third switch and a third node, the third capacitor coupled between the third node and the ground terminal;
a fourth switch coupled to the integrator;
a fourth resistor coupled between the fourth switch and a fourth node, the fourth capacitor coupled between the fourth node and the ground terminal; and
a second subtractor coupled to the third node and the fourth node.

6. The circuit of claim 5 further comprising:
a multiplexer coupled to the first subtractor and the second subtractor;
an analog to digital converter (ADC) coupled to the multiplexer; and
a processor coupled to the ADC.

7. The circuit of claim 1 further comprising a photodiode coupled to the integrator through a pixel switch, the photodiode configured to generate the input signal in response to received light pulses, the photodiode comprising:
a sensor configured to receive the light pulses; and
an associated capacitor configured to store the input signal generated in response to the received light pulses.

8. The circuit of claim 6 configured to operate in a reset phase, an offset phase, a signal phase and a delayed signal phase, wherein in the reset phase:
the reset switch is closed; and
the first switch, the second switch and the third switch are opened.

9. The circuit of claim 8, wherein in the offset phase:
the reset switch is opened, a residual noise is sampled on the feedback capacitor which generates a sampled reset noise voltage at the output terminal of the amplifier;
the pixel switch, the second switch, the third switch and the fourth switch are opened; and
the first switch is closed, so the sampled reset noise voltage is sampled on the first capacitor, and a voltage at the first node is the sampled reset noise voltage.

10. The circuit of claim 8, wherein in the signal phase:
the reset switch remains open;
the first switch is opened;
the pixel switch, the second switch, the third switch and the fourth switch are closed, and the input signal from the photodiode is provided to the integrator which generates a first voltage that is sampled on the second, third and fourth capacitor; and
the second switch and the third switch are opened, and a voltage at each of the second node and the third node is the first voltage.

11. The circuit of claim 10, wherein in the delayed signal phase:
the pixel switch is opened;
the integrator generates a second voltage that is sampled on the fourth capacitor, and a voltage at the fourth node is the second voltage; and
the fourth switch is opened.

12. The circuit of claim 11, wherein:
the first sampling network generates the signal voltage by subtracting the sampled reset noise voltage from the first voltage in the first subtractor;
the second sampling network generates the pixel sampled noise voltage by subtracting the first voltage from the second voltage in the second subtractor;
the ADC generates a first and a second digital signal in response to the signal voltage and the pixel sampled noise voltage respectively; and
the processor stores the first and the second digital signal.

13. The circuit of claim 12, wherein the processor subtracts the second digital signal generated in the previous cycle from the first digital signal generated in the current cycle to generate the true signal voltage.

14. The circuit of claim 12, wherein the second voltage is a sum of the first voltage and the pixel sampled noise voltage, the pixel sampled noise voltage is proportional to a noise associated with the integrator and a noise associated with the pixel switch.

15. A method comprising:
generating a first voltage on receiving an input signal through a pixel switch;
sampling the first voltage on a second capacitor in a first sampling network and on a third capacitor and a fourth capacitor in a second sampling network;
generating a signal voltage from the first voltage by the first sampling network;
generating a second voltage when the pixel switch is opened;
sampling the second voltage on the fourth capacitor in the second sampling network;
generating a pixel sampled noise voltage from the first voltage and the second voltage by the second sampling network; and
subtracting the pixel sampled noise voltage generated in a previous cycle from the signal voltage generated in a current cycle to generate a true signal voltage.

16. The method of claim 15, wherein generating the signal voltage further comprises:
sampling a residual noise on a feedback capacitor to generate a sampled reset noise voltage;
sampling the sampled reset noise voltage on a first capacitor in the first sampling network; and
subtracting the sampled reset noise voltage from the first voltage.

17. The method of claim 15 further comprising generating the input signal by a photodiode in response to received light pulses and the photodiode is coupled to the pixel switch.

18. The method of claim 15, wherein generating the pixel sampled noise voltage further comprises subtracting the first voltage from the second voltage.

19. The method of claim 15 further comprising providing the input signal to an integrator to generate the first voltage, wherein the pixel sampled noise voltage is proportional to a noise associated with the integrator and a noise associated with the pixel switch.

20. An imaging system comprising:
an x-ray source configured to generate x-rays;
an object configured to receive x-rays from the x-ray source, the x-rays pass through the object; and
a receiver configured to receive attenuated x-rays from the object, the receiver comprising a plurality of detectors, and at least one detector of the plurality of detectors comprising:
an integrator configured to receive an input signal;

a first sampling network coupled to the integrator and configured to generate a signal voltage, the first sampling network having a first capacitor and a second capacitor; and a second sampling network coupled to the integrator and configured to generate a pixel sampled noise voltage, the second sampling network having a third capacitor and a fourth capacitor, wherein the pixel sampled noise voltage generated in a previous cycle is subtracted from the signal voltage generated in a current cycle to generate a true signal voltage.

\* \* \* \* \*